(12) United States Patent
Sankai

(10) Patent No.: US 11,925,437 B2
(45) Date of Patent: Mar. 12, 2024

(54) PHOTOACOUSTIC IMAGING APPARATUS AND PHOTOACOUSTIC IMAGING METHOD

(71) Applicants: CYBERDYNE INC., Tsukuba (JP); UNIVERSITY OF TSUKUBA, Tsukuba (JP)

(72) Inventor: Yoshiyuki Sankai, Tsukuba (JP)

(73) Assignee: CYBERDYNE INC., UNIVERSITY OF TSUKUBA, Ibaraki (JP)

( * ) Notice: Subject to any disclaimer, the term of this patent is extended or adjusted under 35 U.S.C. 154(b) by 614 days.

(21) Appl. No.: 17/263,178

(22) PCT Filed: Jul. 24, 2019

(86) PCT No.: PCT/JP2019/029112
§ 371 (c)(1),
(2) Date: Jan. 26, 2021

(87) PCT Pub. No.: WO2020/022409
PCT Pub. Date: Jan. 30, 2020

(65) Prior Publication Data
US 2021/0177270 A1  Jun. 17, 2021

(30) Foreign Application Priority Data
Jul. 26, 2018  (JP) .................................. 2018-140528

(51) Int. Cl.
*A61B 5/00* (2006.01)
(52) U.S. Cl.
CPC .......... *A61B 5/0095* (2013.01); *A61B 5/6801* (2013.01)
(58) Field of Classification Search
CPC ............................ A61B 5/0095; A61B 5/6801
See application file for complete search history.

(56) References Cited

U.S. PATENT DOCUMENTS

| 2015/0038845 A1 | 2/2015 | Agano |
| 2015/0148655 A1 | 5/2015 | Haupt et al. |

FOREIGN PATENT DOCUMENTS

| JP | 2015-029550 A | 2/2015 |
| JP | 2016-537136 A | 12/2016 |
| WO | 2013/064740 A1 | 5/2013 |

OTHER PUBLICATIONS

International Search Report, PCT/JP2019/029112, dated Sep. 3, 2019, 1 pg.

(Continued)

*Primary Examiner* — Rochelle D Turchen
(74) *Attorney, Agent, or Firm* — Volpe Koenig

(57) ABSTRACT

A photoacoustic imaging apparatus comprises: a light emitting unit emitting pulsed light with a wavelength absorbed inside a subject; a thin, flexible film applied to a skin surface of the subject to make the pulsed light transmit it and reflects the light on its outer surface at the same time; a multi-directional light emitting unit emitting a plurality of visible light beams from multi-directions to the outer surface of the thin film; a micro-vibration detection unit detects, on the basis of diffraction and/or interference of a plurality of reflected light obtained from the outer surface of the thin film, a state of causing micro-vibrations of the thin film as the photoacoustic waves generated from the light absorber collide against an inner backside of the thin film; and a shape image transformation unit that produces the images of a shape of the light absorber as detected by the micro-vibration detection unit.

8 Claims, 6 Drawing Sheets

1 PHOTOACOUSTIC IMAGING APPARATUS

(56) References Cited

OTHER PUBLICATIONS

Extended European Search Report dated Mar. 9, 2022 for European Patent Application No. 19841768.5.
Huynh et al., "Photoacoustic imaging using an 8-beam Fabry-Perot scanner," Proc. of SPIE vol. 9708 97082L (2016).
Jathoul et al., "Deep in vivo photoacoustic imaging of mammalian tissues using a tyrosinase-based genetic reporter," Nature Photon 9, pp. 1-8 (2015).
Laufer et al., "In vivo preclinical photoacoustic imaging of tumor vasculature development and therapy," J. Biomed. Opt. 17(5) 056016 (May 21, 2012).

1 PHOTOACOUSTIC IMAGING APPARATUS

FIG. 5
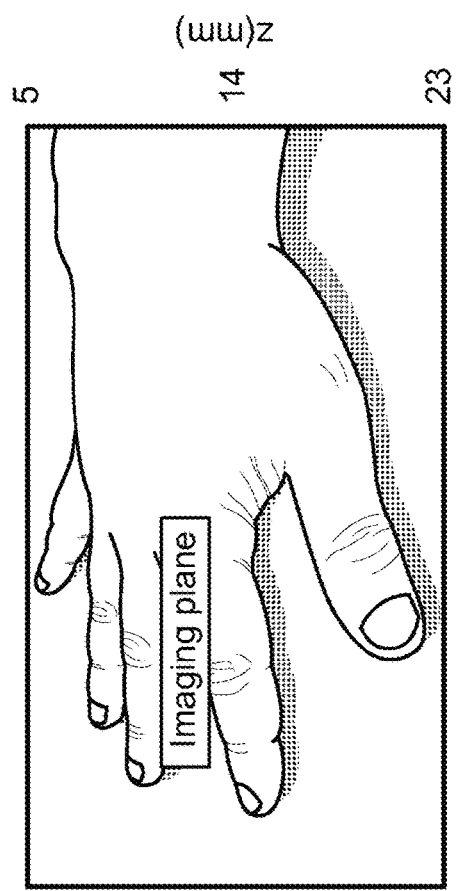
(A)
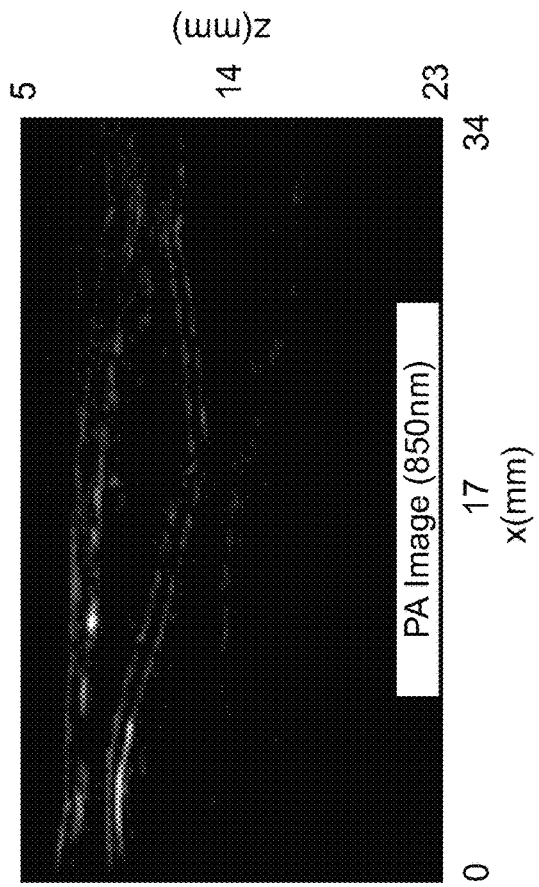
(B)

PHOTOACOUSTIC IMAGING APPARATUS AND PHOTOACOUSTIC IMAGING METHOD

TECHNICAL FIELD

The present invention relates to a photoacoustic imaging technology that detects and images photoacoustic waves generated from a light absorber inside a subject by irradiating the subject with light.

BACKGROUND ART

In recent years, there is proposed a photoacoustic imaging apparatus, as the photoacoustic imaging technology or a photoacoustic tomography technology, that includes an LED light source unit for irradiating a subject with pulsed light and an ultrasonic wave detector for detecting acoustic waves as ultrasonic waves generated by an object inside the subject (see PTL 1).

Moreover, there is also proposed an ultrasonic wave image generation system for generating ultrasonic wave images of the structure inside a patient by scanning over a body surface with a laser source at a sonic speed, transmitting a plurality of acoustic disturbances, and thereby causing propagating photoacoustic waves so that vibrations generated by backward scattering of associated waves obtained by coherent addition of the above-mentioned propagating photoacoustic waves are detected on the surface of the patient (see PTL 2).

Furthermore, there is also proposed a method for detecting skeletal vibrations of electromagnetic waves by using an optical detection method such as an optical interferometry, an optical coherence tomography, or a laser Doppler vibrometer (see PTL 3).

CITATION LIST

Patent Literature

PTL 1: Japanese Patent Application Laid-Open (Kokai) Publication No. 2015-29550
PTL 2: Japanese Patent Application Laid-Open (Kokai) Publication No. 2016-537136
PTL 3: WO 2013/064740

SUMMARY OF THE INVENTION

Problems to be Solved by the Invention

Meanwhile, regarding the photoacoustic imaging technology of PTL 1, the subject is irradiated contactlessly with an LED light; and since imaging by light scattering is measured with an ultrasonic probe, it is necessary to make the probe directly contact the skin.

Moreover, PTL 2 is a method of measuring vibrations of the skin by directly using a laser vibrometer. So, if downy hair, lentigines, pimples, scars, and so on exist on the skin surface, it becomes very difficult to perform fine level measurements.

Furthermore, PTL 3 is different as it performs light irradiation using a laser or pulsed laser light source for the sake of the photoacoustic effect of generating the ultrasonic waves from human tissues; and the detection of the skeletal vibrations is conducted by using at least any one of an optical interferometer, a light interference tomographic imaging apparatus, and the laser Doppler vibrometer. So, the problem similar to that of the above-mentioned PTL 2 still remains.

The present invention was devised in consideration of the above circumstances and aims at proposing a photoacoustic imaging apparatus and a photoacoustic imaging method which are capable of acquiring high-resolution images of the inside of the subject contactlessly and in real time.

Means to Solve the Problems

In order to solve the above-described problems, provided according to the present invention is a photoacoustic imaging apparatus for detecting photoacoustic waves generated from a light absorber inside a subject and producing images of the light absorber on the basis of the photoacoustic waves, wherein the photoacoustic imaging apparatus includes: a light emitting unit that emits pulsed light with a wavelength absorbed inside the subject; a thin film that is pasted or applied to a skin surface of the subject, has flexibility as a whole, and makes the pulsed light transmit it and reflects the light on its outer surface at the same time; a multi-directional light emitting unit that emits a plurality of visible light beams at the same time from multi-directions to the outer surface of the thin film; a micro-vibration detection unit that detects, on the basis of diffraction and/or interference of a plurality of reflected light obtained from the outer surface of the thin film, a state of causing micro-vibrations of the thin film as the photoacoustic waves generated from the light absorber collide against an inner backside of the thin film; and a shape image transformation unit that produces the images of a shape of the light absorber on the basis of a vibrational state of the thin film as detected by the micro-vibration detection unit.

This photoacoustic imaging apparatus can acquire high-resolution images contactlessly and in real time by irradiating the thin film, which is caused by the photoacoustic waves generated from the light absorber inside the subject to perform the micro-vibrations, with the light from outside and measuring the diffraction and/or the interference of the reflected light.

Moreover, according to the present invention, the micro-vibration detection unit eliminates sound disturbance which occurs as a result of multiple reflections of the photoacoustic waves on an inner backside of the thin film, on the basis of time difference timing between an occurrence time point of the photoacoustic waves from the light absorber and arrival time of the photoacoustic waves to the inner backside of the thin film. As a result, the photoacoustic imaging apparatus can produce the images of the shape of the light absorber inside the subject accurately according to how much the sound disturbance is eliminated.

Furthermore, according to the present invention, film coating is applied to the inner backside of the thin film to eliminate an air layer between the thin film and the skin surface and a regular or irregular uneven pattern is applied to the outer surface of the thin film. As a result, with the photoacoustic imaging apparatus, the photoacoustic waves directly reach the thin film without attenuating in the air layer between the subject's skin and the thin film, so that the photoacoustic waves can be accurately transformed to the micro-vibrations of the thin film. Then, as the micro-vibrations of the thin film are reflected in the regular or irregular uneven pattern, there is an advantageous effect of making it much easier to measure the diffraction and/or the interference of the reflected light of the light emitted from outside.

Furthermore, according to the present invention, the shape image transformation unit stores a reflected light group, which is obtained as the plurality of visible light beams emitted from the multi-directional light emitting unit reflect on the outer surface of the reflective thin film, as a test pattern in advance and performs calibration to correct image quality fluctuations according to the uneven pattern of the thin film on the basis of the test pattern. As a result, the photoacoustic imaging apparatus can obtain high-resolution images based on the micro-vibrations of the thin film no matter how the uneven pattern of the thin film is formed, whether regularly or irregularly.

Furthermore, provided according to the present invention is a photoacoustic imaging method for detecting photoacoustic waves generated from a light absorber inside a subject and producing images of the light absorber on the basis of the photoacoustic waves, wherein the photoacoustic imaging method includes: a first step of emitting pulsed light with a wavelength absorbed inside the subject; a second step of emitting a plurality of visible light beams at the same time from multi-directions to an outer surface of a thin film which is pasted or applied to a skin surface of the subject, has an elastic force as a whole, and makes the pulsed light transmit it and reflects the light on its outer surface at the same time; a third step of detecting, on the basis of diffraction and/or interference of a plurality of reflected light obtained from the outer surface of the thin film, a state of causing micro-vibrations of the thin film as the photoacoustic waves generated from the light absorber collide against an inner backside of the thin film; and a fourth step of producing the images of a shape of the light absorber on the basis of the detected vibrational state of the thin film.

By this photoacoustic imaging method, the high-resolution images can be acquired contactlessly and in real time by irradiating the thin film, which is caused by the photoacoustic waves generated from the light absorber inside the subject to perform the micro-vibrations, with the light from outside and measuring the diffraction and/or the interference of the reflected light.

Advantageous Effects of the Invention

The photoacoustic imaging apparatus and the photoacoustic imaging method which are capable of acquiring high-resolution images of the inside of the subject contactlessly and in real time can be realized according to the present invention.

BRIEF DESCRIPTION OF DRAWINGS

FIG. 5A and FIG. 5B are a conceptual diagram and a measured drawing showing the photoacoustic imaging results when the subject is a human's fingers.

DESCRIPTION OF EMBODIMENTS

An embodiment of the present invention will be described below in detail with reference to the drawings.

Figure 1:
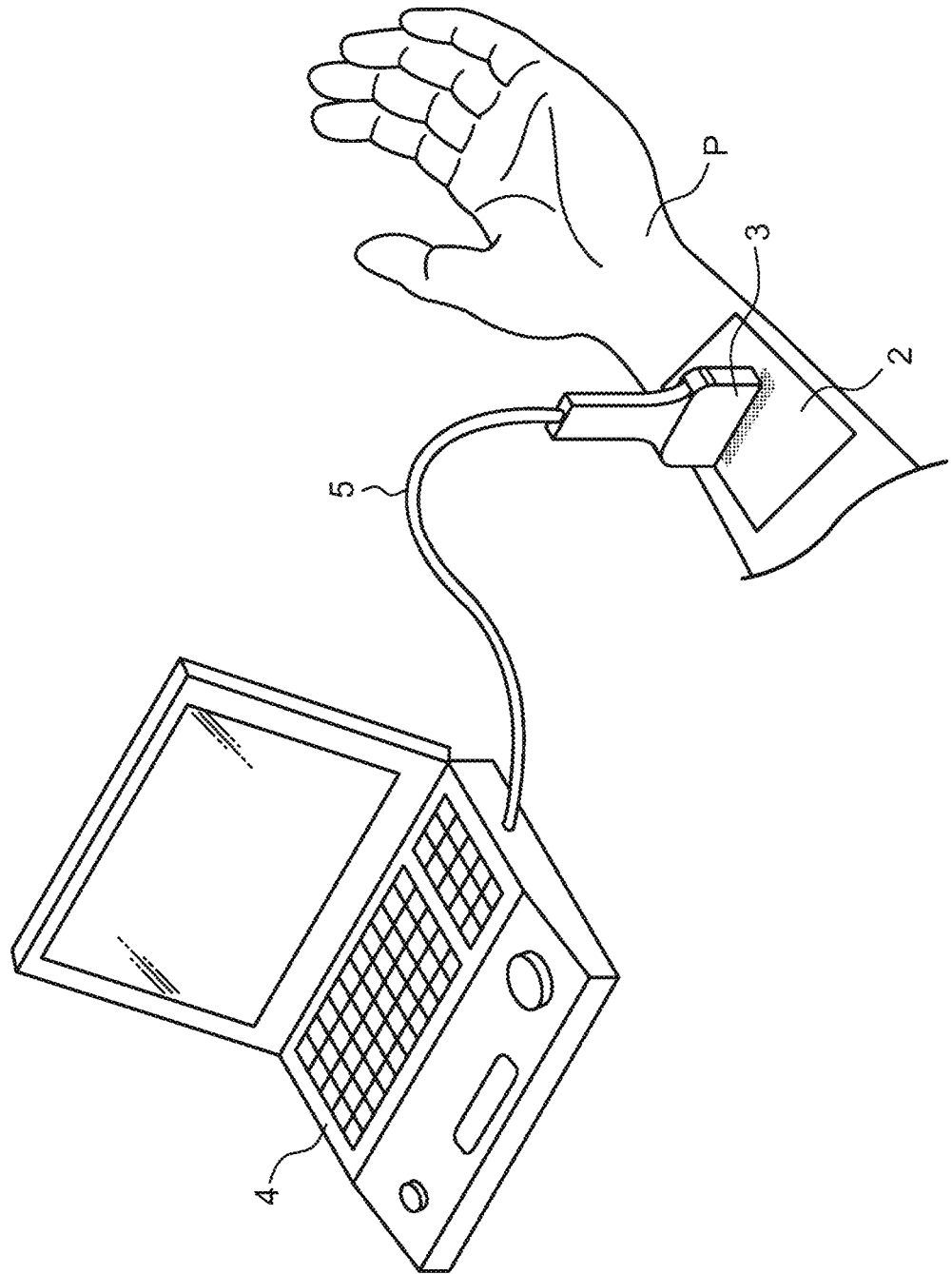
FIG. 1 is an external appearance perspective view illustrating the configuration of a photoacoustic imaging apparatus according to this embodiment.

(1) Configuration of Photoacoustic Imaging Apparatus According to this Embodiment FIG. 1 is a schematic external appearance view of a photoacoustic imaging apparatus 1 according to this embodiment. This photoacoustic imaging apparatus 1 is configured so that a specified optical characteristic thin film 2 is pasted on a skin surface corresponding to an object (light absorber) inside a subject P; and photoacoustic waves are caused to be generated from the object which is irradiated with light via the optical characteristic thin film 2; and a probe unit (photoacoustic wave detection unit) 3 which optically detects a vibrational state of the optical characteristic thin film 2, which is caused by the photoacoustic waves to perform the micro-vibrations, and an apparatus main body 4 which produces images by processing a signal detected by the probe unit 3 are coupled together via a cable 5.

When an operator keeps holding the probe unit 3 and locates it on the surface of the subject (such as a human body surface) P contactlessly and causes an object (such as blood vessels, nerve tissues, and tumors) of the subject P to be irradiated with light via the optical characteristic thin film 2, optical absorption of the object causes particular molecules in vivo to enter an excited state and heat occurs when the excited state returns to a steady state. When photoacoustic waves of the molecules which are caused by a temperature difference (thermal expansion) of the surroundings reach the skin from the object, they cause the optical characteristic thin film 2, which contacts the surface of the skin, to vibrate.

Figure 2:
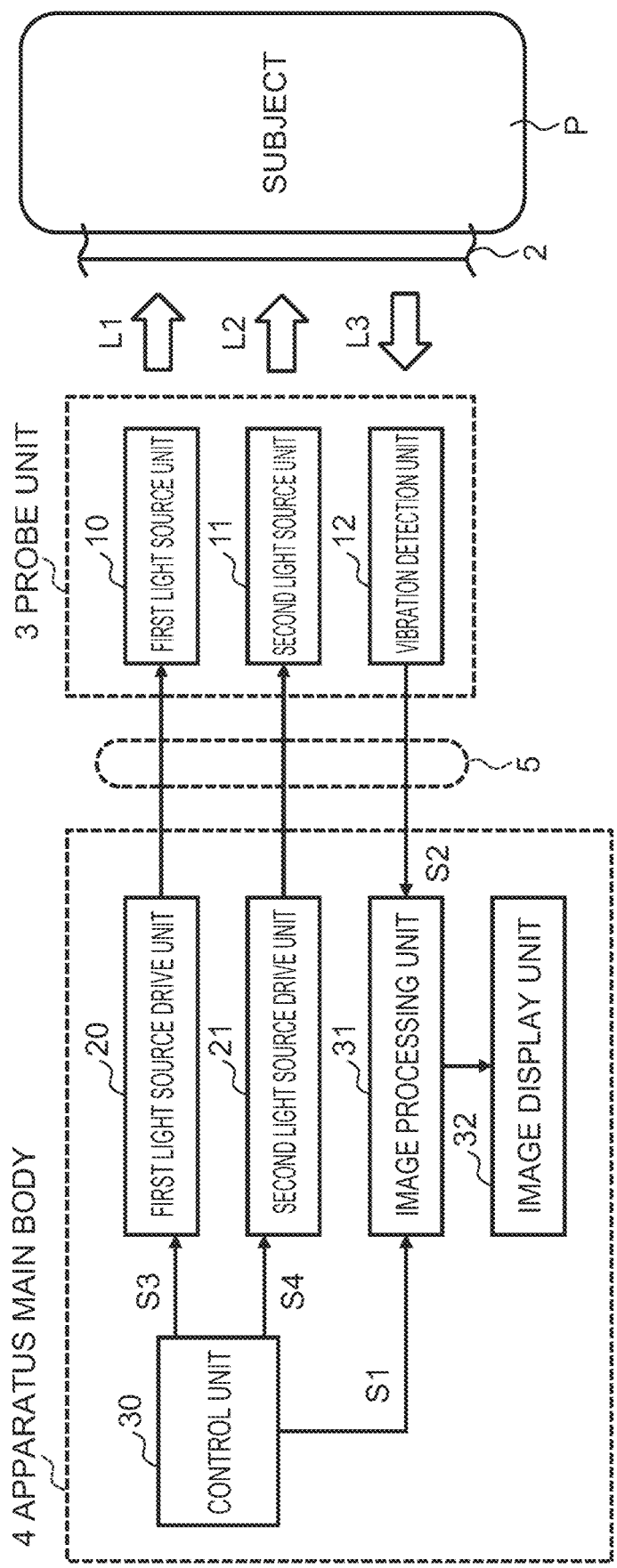
FIG. 2 is a block diagram illustrating an internal configuration of the photoacoustic imaging apparatus according to this embodiment.

FIG. 2 illustrates an internal configuration of the photoacoustic imaging apparatus 1. The probe unit 3 includes: a first light source unit (light emitting unit) 10 in which a plurality of light emitting diode devices (not shown) are serially connected and arranged; a second light source unit (multi-directional light emitting unit) 11 configured of a plurality of visible light emitting diode devices (not shown) for emitting visible light to the optical characteristic thin film 2 from multi-directions; and a vibration detection unit (micro-vibration detection unit) 12 that detects the micro-vibrations of the optical characteristic thin film 2.

The first light source unit 10 discharges pulsed light L1, which has a wavelength of an infrared-region (for example, the wavelength of approximately 850 [nm]), from each of the plurality of light emitting diode devices according to an electric current supplied from the first light source drive unit 20, thereby irradiating the subject P with each pulsed light beam L1. Incidentally, it is designed so that images of only a desired object can be produced by setting the wavelength of the pulsed light L1 in advance according to the object type (a light absorber such as hemoglobin, blood vessels, nerve tissues, or tumors) of the subject P.

Figure 3:
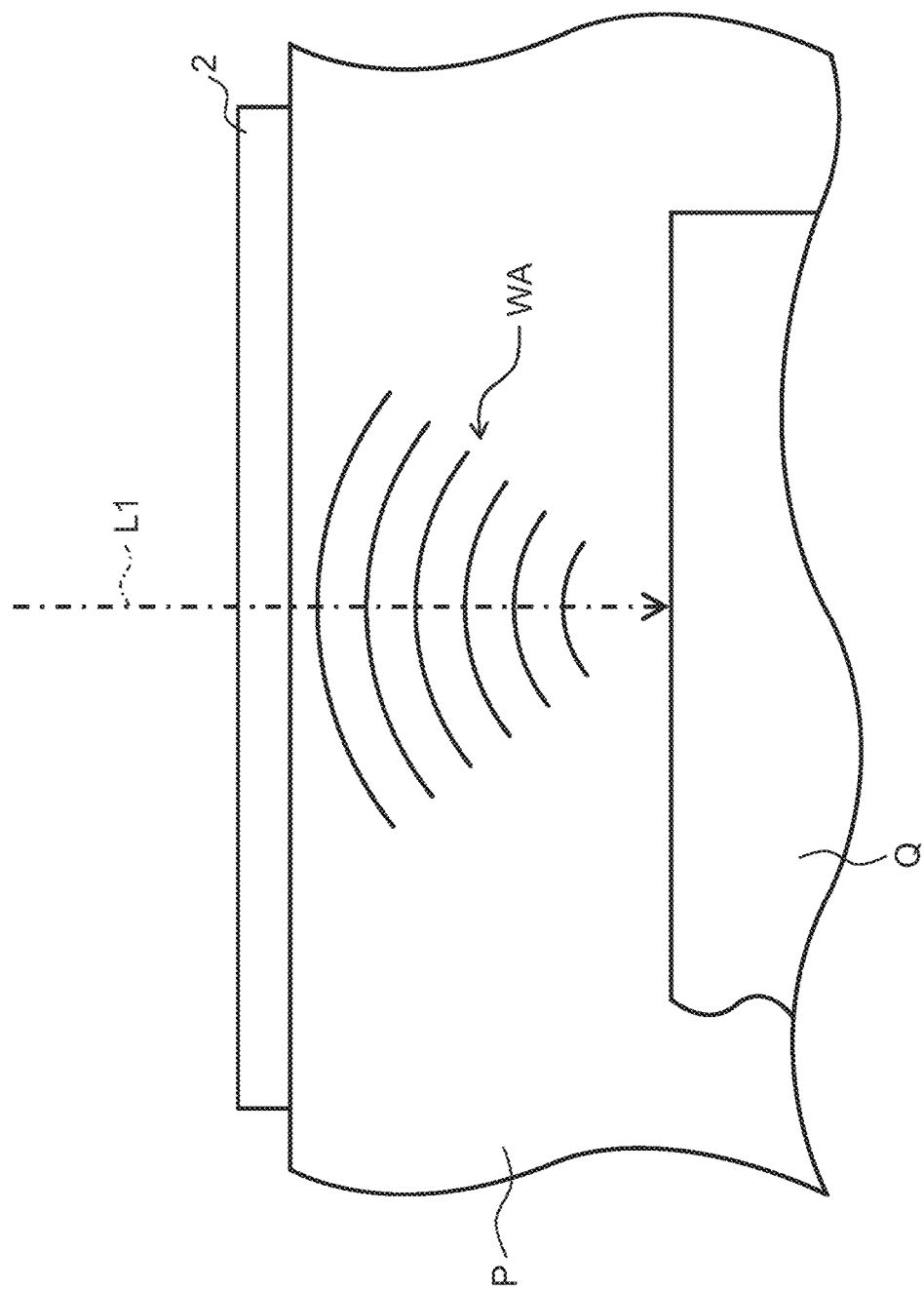
FIG. 3 is a schematic diagram showing a state where an LED light is emitted to an object of a subject via an optical characteristic thin film.

Then, as illustrated in FIG. 3, the pulsed light L1 emitted from the first light source unit 10 of the probe unit 3 to the subject P is absorbed by the object (light absorber) Q inside the subject P. The object Q expands or contracts (returns from the expanded size to its original size) according to irradiation intensity (absorbed amount) of the pulsed light L1, thereby generating the photoacoustic waves WA from the object Q.

Figure 4:
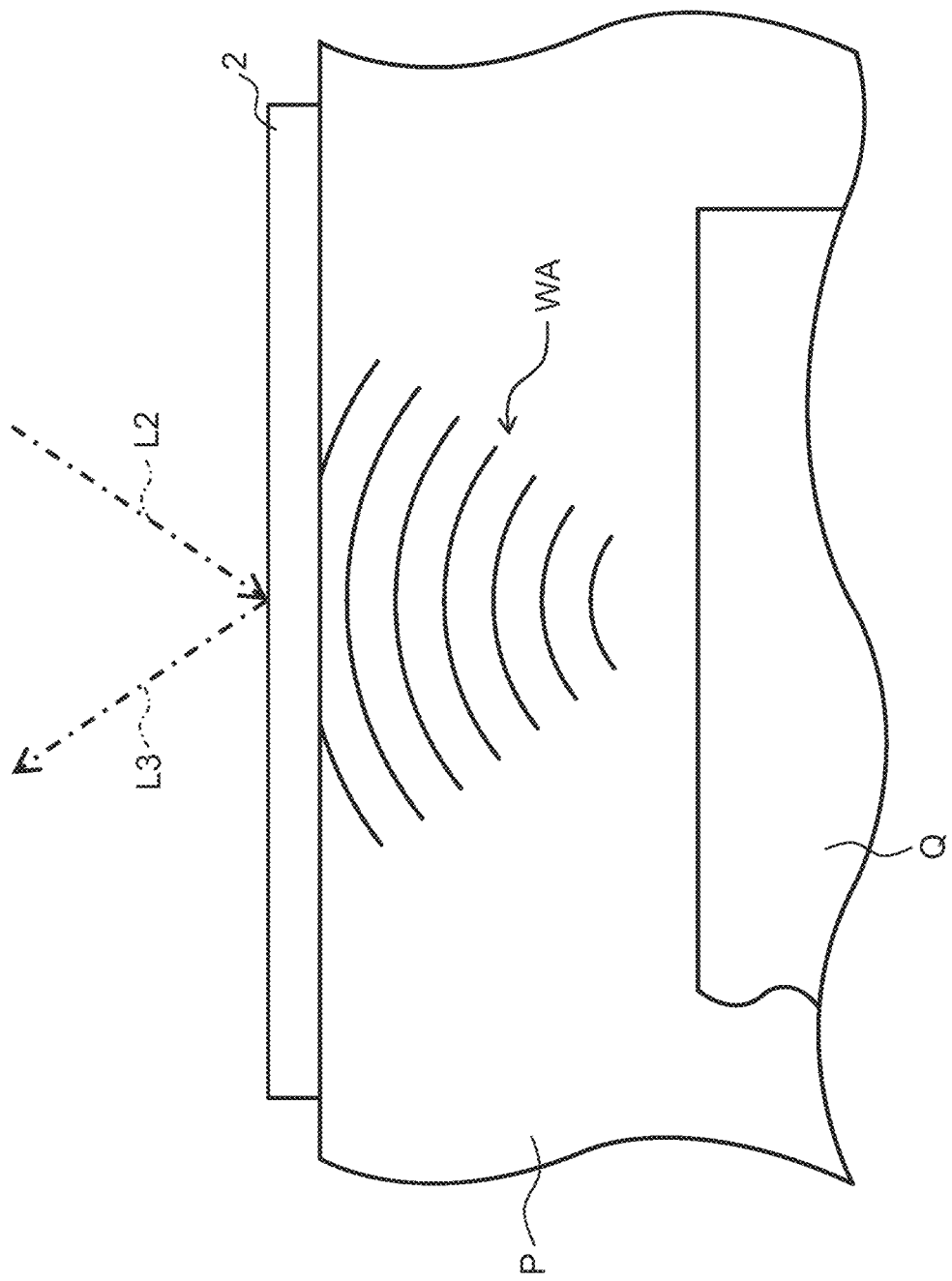
FIG. 4 is a schematic diagram showing a micro-vibration state of the optical characteristic thin film which is caused by photoacoustic waves generated from inside the subject.

Referring to FIG. 4, the second light source unit 11 emits visible light L2 from multi-directions from the plurality of visible light emitting diode devices to the optical characteristic thin film 2 according to an electric current supplied from the second light source drive unit 21, thereby generating reflected light L3 from the optical characteristic thin film 2 which is performing micro-vibrations. The vibration detection unit 12 detects, on the basis of diffraction and/or interference of the plurality of reflected light beams L3 obtained from the outer surface of the optical characteristic thin film 2, a state where the photoacoustic waves WA generated from the object (light absorber) Q collide against the back inner surface of the optical characteristic thin film 2 and thereby causes the optical characteristic thin film 2 to perform the micro-vibrations.

The apparatus main body 4 includes a control unit 30 for controlling the first light source drive unit 20 and the second light source drive unit 21, respectively, and an image processing unit 31 (they are collectively referred to as a "shape image transformation unit"). The image processing unit 31 acquires images with the resolution corresponding to the object (tomographic images based on acoustic waves) in real time on the basis of a sampling trigger signal S1 transmitted from the control unit 30 and a detection signal S2 indicating the detection result obtained from the vibration detection unit 12 of the probe unit 3 and displays the images on an image display unit 32 composed of a liquid crystal panel or the like.

Moreover, the control unit 30 is designed to control driving of the light irradiation by sending respectively different trigger signals to the first light source drive unit 20 and the second light source drive unit 21. The first light source drive unit 20 emits pulsed light with specified width and frequency from each of the plurality of light emitting diode devices by generating a direct current from electric power supplied from an external power source (not shown) and turning on or off a switch composed of, for example, an FET (Field Effect Transistor) on the basis of a pulsed trigger signal S3 from the control unit 30.

The second light source drive unit 21 generates a direct current from the electric power supplied from the external power source (not shown) and causes the plurality of visible light emitting diode devices to emit the steady visible light L2 from the multi-directions on the basis of a trigger signal S4 from the control unit 30. Basically, the second light source drive unit 21 is controlled by the control unit 30 so that it is driven only when the first light source drive unit 20 is driven.

Incidentally, the control unit 30 in the apparatus main body 4 causes the vibration detection unit 12 to measure time difference timing between an occurrence time point of the photoacoustic waves from the object (light absorber) and arrival time of the photoacoustic waves at the inner backside of the optical characteristic thin film 2, so that the control unit 30 can eliminate the sound disturbance which occurs as a result of the multiple reflections of the photoacoustic waves on the inner backside of the optical characteristic thin film 2 according to the above-described time difference timing.

Particularly, since the LED light is pulsed light with the frequency band of 20 [MHz], the sound disturbance can be eliminated only by measuring the time difference timing between the occurrence time point of a first wave from the object (light absorber) and the time point when the optical characteristic thin film vibrates.

(2) Configuration of Optical Characteristic Thin Film

This optical characteristic thin film 2 is a light-transmittance-controlled film which is pasted or applied to the skin surface of the subject P, is formed from polymer materials having flexibility as a whole, and makes the LED light transmit through it and reflects the light on its outer surface at the same time.

As materials for this optical characteristic thin film 2, for example, the following synthetic resins having permeability can be used: polyethylene terephthalate (PET), polycarbonate, acrylic resins such as polymethyl methacrylate, styrene resins, polyvinyl chloride, and acrylic-styrene copolymers.

Practically, the optical characteristic thin film 2 is configured to transmit the light which has entered at a specified angle, among the light emitted from the first light source unit 10 and the second light source unit and reflect the light which has entered at an angle other than the above-mentioned angle among the entered light. In a case of this embodiment, the optical characteristic thin film 2 is configured so that it transmits only the pulsed light emitted from the first light source unit 10, while it reflects the visible light emitted from the second light source unit 11.

Specifically, regarding the optical characteristic thin film 2, its light incidence plane is formed as a flat plane and a prism array is disposed on its light exit plane side. Regarding optical effects of the optical characteristic thin film 2, a combination of the following can be obtained: a light refraction action when the flat incidence plane guides the light beams from a low refraction side to a high refraction side; and a light recursive effect by refraction and total reflection on the exit plane (the prism array) which contacts the skin surface. Incidentally, for example, a lenticular lens in which a lens is provided, or a cylindrical lens with an aspheric-shaped section may be applied instead of the prism array structure.

Furthermore, regarding the optical characteristic thin film 2, the reflected light to implement the light recursive effect is obtained from the incident light from the multi-directions. So, when the light interference occurs, it becomes possible to detect, on the basis of the interference of the received light, the state where the interfered light collides against the back surface of the optical characteristic thin film 2 and causes the thin film itself to perform micro-vibrations.

Furthermore, regarding the optical characteristic thin film 2, film coating such as an oil film or a transparent gel is applied to between its inner backside and the skin surface, so that it becomes possible to directly cause the optical characteristic thin film 2 to vibrate without making the photoacoustic waves, which have reached from the object to the skin, attenuated by the air layer and, as a result, produce images of the shape of the object with high accuracy.

Figure 6:
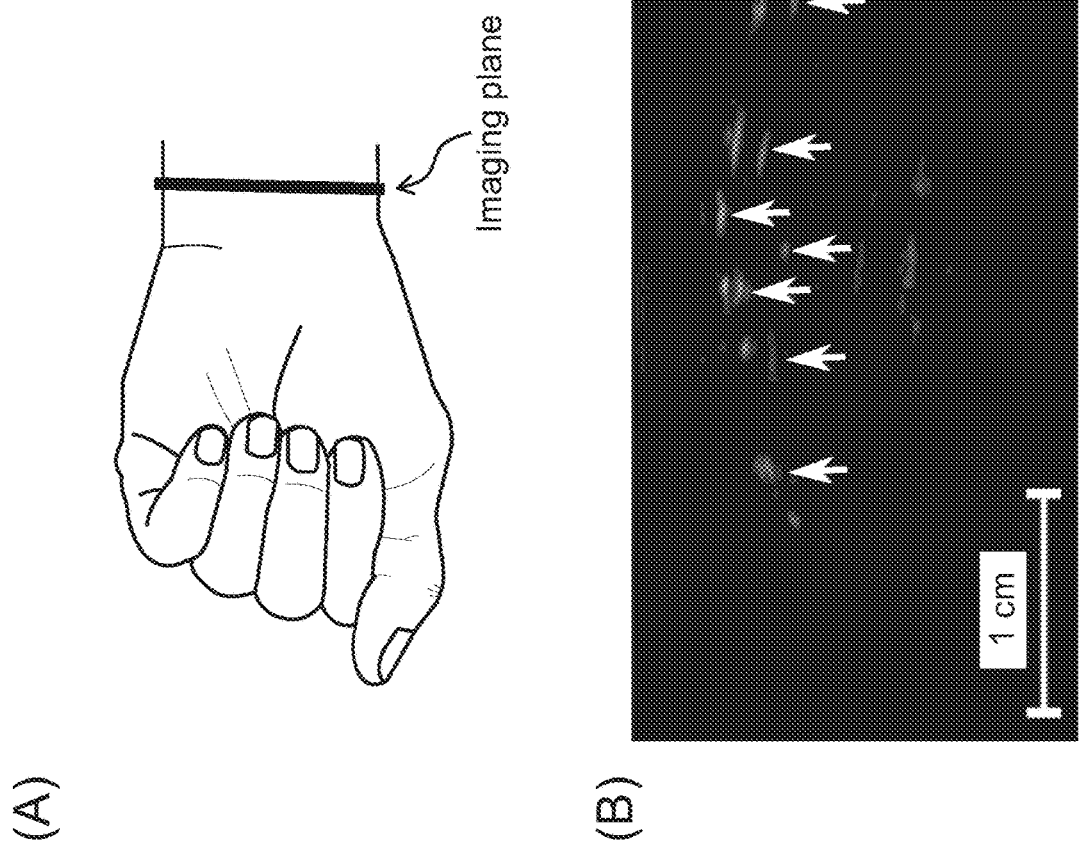
FIG. 6A and FIG. 6B are a conceptual diagram and a measured drawing showing the photoacoustic imaging results when the subject is a human's wrist.

Practically, in a case as illustrated in FIG. 5A where the subject P is a human's fingers and the object is blood vessels, an image of the imaging result obtained by using the photoacoustic imaging apparatus 1 is indicated as in FIG. 5B. Similarly, in a case as illustrated in FIG. 6A where the subject P is a human's wrist and the object is blood vessels, an image of the imaging result obtained by using the photoacoustic imaging apparatus 1 is indicated as in FIG. 6B.

(3) Other Embodiments

Incidentally, this embodiment has described the case where the surface of the optical characteristic thin film 2 is formed as a flat surface; however, the present invention is not limited to this example and a regular or irregular uneven pattern or a mesh shape may be formed on the outer surface of the optical characteristic thin film. In this case, the reflected light relative to the incident light from the multi-directions is diffracted at the optical characteristic thin film, so that it becomes possible to detect, on the basis of the received diffracted light, the state where the diffracted light collide against the back surface of the optical characteristic thin film and cause the thin film itself to perform micro-vibrations. Furthermore, the micro-vibrations of the optical characteristic thin film may be detected by combining this diffracted light with the interference light caused by the plurality of reflected light beams according to this embodiment.

Furthermore, this embodiment has described the case where the micro-vibrations of the optical characteristic thin film 2 are directly detected on the basis of the diffraction and/or the interference of the plurality of reflected light beams by the second light source unit 11; however, the present invention is not limited to this example and preliminary measures may be taken to enhance the detection accuracy of the optical characteristic thin film.

For example, the control unit 30 for the apparatus main body 4 stores a reflected light group, which is obtained as the plurality of visible light beams emitted from the second light source unit 11 for the probe unit 3 reflect on the outer surface of the optical characteristic thin film 2, as a test pattern in advance and performs calibration to correct image quality fluctuations according to the outer surface shape (such as the uneven pattern or the mesh shape) of the optical characteristic thin film 2 on the basis of the test pattern. As a result, when the optical characteristic thin film 2 having flexibility (elasticity) is pasted or applied to the skin surface of the subject P, it becomes possible to correct the image quality fluctuations when producing images of the shape of the object as long as the calibration is performed in advance no matter in what condition of the outer surface shape the optical characteristic thin film is attached to the skin surface.

Some embodiments have been explained above; however, they are exemplified to explain the present invention and are not intended to limit the scope of the present invention to only these embodiments. The present invention can be executed in other various forms.

REFERENCE SIGNS LIST

1: photoacoustic imaging apparatus
2: optical characteristic thin film
3: probe unit
4: apparatus main body
5: cable
10: first light source unit
11: second light source unit
12: vibration detection unit
20: first light source drive unit
21: second light source drive unit
30: control unit
31: image processing unit
32: image display unit
P: subject

The invention claimed is:

1. A photoacoustic imaging apparatus for detecting photoacoustic waves generated from a light absorber inside a subject and producing images of the light absorber on the basis of the photoacoustic waves, the photoacoustic imaging apparatus comprising:

a light emitting unit that emits pulsed light with a wavelength absorbed inside the subject;
a thin film that is pasted or applied to a skin surface of the subject, has flexibility as a whole, and makes the pulsed light transmit it and reflects the light on its outer surface at the same time;
a multi-directional light emitting unit that emits a plurality of visible light beams at the same time from multi-directions to the outer surface of the thin film;
a micro-vibration detection unit that detects, on the basis of diffraction and/or interference of a plurality of reflected light obtained from the outer surface of the thin film, a state of causing micro-vibrations of the thin film as the photoacoustic waves generated from the light absorber collide against an inner backside of the thin film; and
a shape image transformation unit that produces the images of a shape of the light absorber on the basis of a vibrational state of the thin film as detected by the micro-vibration detection unit.

2. The photoacoustic imaging apparatus according to claim 1,
wherein the micro-vibration detection unit eliminates sound disturbance which occurs as a result of multiple reflections of the photoacoustic waves on the inner backside of the thin film, on the basis of time difference timing between an occurrence time point of the photoacoustic waves from the light absorber and arrival time of the photoacoustic waves to the inner backside of the thin film.

3. The photoacoustic imaging apparatus according to claim 1,
wherein film coating is applied to the inner backside of the thin film to eliminate an air layer between the thin film and the skin surface and a regular or irregular uneven pattern is applied to the outer surface of the thin film.

4. The photoacoustic imaging apparatus according to claim 3,
wherein the shape image transformation unit stores a reflected light group, which is obtained as the plurality of visible light beams emitted from the multi-directional light emitting unit reflect on the outer surface of the reflective thin film, as a test pattern in advance and performs calibration to correct image quality fluctuations according to the uneven pattern of the thin film on the basis of the test pattern.

5. A photoacoustic imaging method for detecting photoacoustic waves generated from a light absorber inside a subject and producing images of the light absorber on the basis of the photoacoustic waves, the photoacoustic imaging method comprising:

a first step of emitting pulsed light with a wavelength absorbed inside the subject;
a second step of emitting a plurality of visible light beams at the same time from multi-directions to an outer surface of a thin film which is pasted or applied to a skin surface of the subject, has an elastic force as a whole, and makes the pulsed light transmit it and reflects the light on its outer surface at the same time;
a third step of detecting, on the basis of diffraction and/or interference of a plurality of reflected light obtained from the outer surface of the thin film, a state of causing micro-vibrations of the thin film as the photoacoustic waves generated from the light absorber collide against an inner backside of the thin film; and a fourth step of producing the images of a shape of the light absorber on the basis of the detected vibrational state of the thin film.

6. The photoacoustic imaging method according to claim 5, wherein in the third step, sound disturbance which occurs as a result of multiple reflections of the photoacoustic waves on the inner backside of the thin film is eliminated on the basis of time difference timing between an occurrence time point of the photoacoustic waves from the light absorber and arrival time of the photoacoustic waves to the inner backside of the thin film.

7. The photoacoustic imaging method according to claim 5, wherein film coating is applied to the inner backside of the thin film to eliminate an air layer between the thin film and the skin surface and a regular or irregular uneven pattern is applied to the outer surface of the thin film.

8. The photoacoustic imaging method according to claim 7, wherein in the fourth step, a reflected light group, which is obtained as the plurality of visible light beams emitted in the second step reflect on the outer surface of the reflective thin film, is stored as a test pattern in advance and calibration is performed to correct image quality fluctuations according to the uneven pattern of the thin film on the basis of the test pattern.

* * * * *